US012656357B2

(12) United States Patent     (10) Patent No.:    US 12,656,357 B2

Joy et al.                    (45) Date of Patent:      Jun. 16, 2026

(54) METHODS AND DEVICES THAT CHANGE COLOR TO INDICATE THE PRESENCE OF OPIOIDS AND OTHER NARCOTICS

(71) Applicant: Abraham Joy, Copley, OH (US)

(72) Inventors: Abraham Joy, Copley, OH (US); Tanmay Jain, Akron, OH (US); Nicholas Nun, Akron, OH (US); Amal Narayanan, Cuyahoga Falls, OH (US); Russell Catania, Mentor, OH (US)

(73) Assignee: The University of Akron, Akron, OH (US)

( * ) Notice: Subject to any disclaimer, the term of this patent is extended or adjusted under 35 U.S.C. 154(b) by 752 days.

(21) Appl. No.: 17/258,789

(22) PCT Filed: Jul. 9, 2019

(86) PCT No.: PCT/US2019/040919

§ 371 (c)(1),
(2) Date: Jan. 8, 2021

(87) PCT Pub. No.: WO2020/014174

PCT Pub. Date: Jan. 16, 2020

(65) Prior Publication Data

US 2021/0302446 A1     Sep. 30, 2021

Related U.S. Application Data

(60) Provisional application No. 62/696,484, filed on Jul. 11, 2018.

(51) Int. Cl.
*G01N 33/94*       (2006.01)
*G01N 21/78*       (2006.01)

(52) U.S. Cl.
CPC ......... *G01N 33/9486* (2013.01); *G01N 21/78* (2013.01); *G01N 33/94* (2013.01)

(58) Field of Classification Search
CPC ..... G01N 33/9486; G01N 21/78; G01N 33/94
See application file for complete search history.

(56) References Cited

U.S. PATENT DOCUMENTS

| | | |
|---|---|---|
| 3,485,706 A | 12/1969 | Evans |
| 3,620,903 A | 11/1971 | Bunting, Jr. et al. |
| 3,849,241 A | 11/1974 | Butin et al. |
| 4,100,324 A | 7/1978 | Anderson et al. |
| 4,340,563 A | 7/1982 | Appel et al. |
| 4,443,513 A | 4/1984 | Meitner et al. |
| 4,511,488 A | 4/1985 | Matta |
| 4,548,856 A | 10/1985 | Ali Khan et al. |
| 4,775,582 A | 10/1988 | Abba et al. |
| 4,833,003 A | 5/1989 | Win et al. |
| 4,853,281 A | 8/1989 | Win et al. |
| 5,009,747 A | 4/1991 | Viazmensky et al. |
| 5,284,703 A | 2/1994 | Everhart et al. |
| 5,350,624 A | 9/1994 | Georger et al. |

| | | |
|---|---|---|
| 5,382,400 A | 1/1995 | Pike et al. |
| 5,575,874 A | 11/1996 | Griesbach, III et al. |
| 5,667,635 A | 9/1997 | Win et al. |
| 6,200,669 B1 | 3/2001 | Marmon et al. |
| 6,224,977 B1 | 5/2001 | Kobylivker et al. |
| 6,750,163 B2 | 6/2004 | Wang et al. |
| 6,811,638 B2 | 11/2004 | Close et al. |
| 6,946,413 B2 | 9/2005 | Lange et al. |
| 6,960,371 B2 | 11/2005 | Bunyard et al. |
| 9,593,201 B2 | 3/2017 | Joy et al. |
| 2004/0192136 A1 | 9/2004 | Gusky et al. |
| 2006/0008621 A1 | 1/2006 | Gusky et al. |
| 2010/0197516 A1 | 8/2010 | Holmes |
| 2011/0151596 A1 | 6/2011 | Cho |
| 2011/0159596 A1* | 6/2011 | Keinan ................ G01N 1/2211 |
| | | 422/86 |
| 2017/0233912 A1 | 8/2017 | Kellner et al. |

OTHER PUBLICATIONS hhs.gov/opioids. [Online]. Available: https://www.hhs.gov/opioids/about-theepidemic/index.html. [Accessed: Sep. 7, 2018].

Opioid Overdoses Treated in Emergency Departments. [Online]. Available: https://www.cdc.gov/vitalsigns/opioid-overdoses/. [Accessed: Sep. 7, 2018].

B. Medsker, E. Fomo, H. Simhan, C. Juan, and R. Sciences, "The Economic Burden of Prescription Opioid Overdose, Abuse and Dependone in the United States, 2013," Med. Care, vol. 54,No. 10,pp. 901-906,2016.

M. P. Prekupec, P. A. Mansky, and M. H. Baumann, "Misuse of Novel Synthetic Opioids: A Deadly New Trend," J. Addict. Mad., vol. 11, No. 4, pp. 256-265, 2017.

J. K. O'Donnell, J. Halpin, C. L. Mattson, B. A. Goldberger, and R. M. Gladden, "Deaths Involving Fentanyl, Fentanyl Analogs, and U-47700 -10 States, Jul.-Dec. 2016," MMWR. Morb. Morla/. Wk/y. Rep., vol. 66, No. 43, pp. 1197-1202, 2017.

"Morbidity and Mortality Weekly Report (MMWR)." [Online]. Available: https://www.cdc.gov/mmwr/volumes/65/wr/mm6533a2. htm. [Accessed: Sep. 7, 2018].

J. K. O'Donnell, R. M. Gladden, and p. Seth, "Trends in Deaths Involving Heroin and Synthetic Opioids Excluding Methadone, and Law Enforcement Drug Product Reports, by Census Region—United States, 2006-2015," MMWR. Morb. Mortal. Wkly. Rep., vol. 66, No. 34,pp. 897-903, 2017.

(Continued)

Primary Examiner — Jennifer Wecker
Assistant Examiner — Steven Ray Castaneda
(74) Attorney, Agent, or Firm — Renner, Kenner, Greive, Bobak, Taylor & Weber

(57) ABSTRACT

A safe and reliable drug detection device is provided that detects the presence of opioids and other amine-containing drugs, and enables first responders, law enforcement personnel, and others to avoid inadvertent exposure to these potentially lethal drugs. The detector device includes a substrate and a dye that produces a visible color change rapidly when the device is brought into contact with an opioid or other amine-containing drug. A method for preparing the detector device and a method for detecting opioids and other amine-containing drugs on a surface are also provided.

20 Claims, No Drawings

(56) References Cited

OTHER PUBLICATIONS

"Fentanyl FAQs." [Online]. Available: https:llwww.dea.gov/druginfo/fentanyl-faq.shtml. [Accessed: Sep. 7, 2018].

P. Armenian, K. T. Vo, J. Barr-Walker, and K. L. Lynch, "Fentanyl, fentanyl analogs and novel synthetic opioids: A comprehensive review," Neuropharmacology, vol. 134, pp. 121-132, 2018.

K. Tsujikawa et al., "Development of an on-site screening system for amphetamine-type stimulant tablets with a portable attenuated total reflection Fourier transform infrared spectrometer," Anal. Chim. Acta, vol. 608, No. 1, pp. 95-103, 2008.

N. W. Tumer, M. Cauchi, E. V. Piletska, C. Preston, and S. A. Piletsky, "Rapid qualitative and quantitative analysis of opiates in extract of poppy head via FTIR and chemometrics: Towards in-field sensors," Biosens. Bioelectron., vol. 24, No. 11, pp. 3322-3328, 2009.

"Powerful detection technology." [Online]. Available: https:llcen. acs.org/articles/95/i451P0werful-detection-technology-powerful-new. html. [Accessed: Sep. 7, 2018].

K. E. Toole, S. Fu, R. G. Shimmon, N. Kraymen, and S. Taflaga, "Color Tests for the Preliminary Identification of Methcathinone and Analogues of Methcathinone," Microgram J., vol. 9, No. 1, pp. 27-32, 2007.

K. M. Agg, A. F. Craddock, R. Bos, P. S. Francis, S. W. Lewis, and N. W. Bamett, "A rapid test for heroin (3,6-diacetylmorphine) based on two chemiluminescence reactions," J. Forensic Sci., vol. 51, No. 5, pp. 108~1084, 2006.

N. A. dos Santos et a/. , "Evaluating the selectivity of colorimetric test (Fast Blue BB salt) for the cannabinoids identification in marijuana street samples by UV-Vis, TLC, ESI(+)FT-ICR MS and ESI(+)MS/MS," Forensic Chern., vol. 1, pp. 13-21, 2016.

M. Philp and S. Fu, "A review of chemical 'spot' tests: A presumptive illicit drug dentification technique," Drug Test. Anal., vol. 10, No. 1, pp. 95-108, 2018.

C. L. O'Neal, D. J. Crouch, and A. A. Fatah, "Validation of Twelve Chemical Spot Tests for the Detection of Drugs of Abuse," Encycl. Forensic Sci. Second Ed., vol. 109, pp. 38~387, 2012.

N. Goonoo, A. Bhaw-Luximon, R. Ujoodha, A. Jhugroo, G. K. Hulse, and D. Jhurry, "Naltrexone: A review of existing sustained drug delivery systems and emerging nanabased systems," J. Control. Release, vol. 183, No. 1, pp. 154-166, 2014.

S. D. Comer, M. A. Sullivan, and G. K. Hulse, "Sustained-release naltrexone: novel treatment for opioid dependence. [Review] [105 refs]," Expert Opin. Investig. Drugs, vol. 16,No. 8,pp. 1285-1294, 2007.

P. Lobmaier, M. Gossop, H. Waal, and J. Bramness, "The pharmacological treatment of opioid addiction—a clinical perspective," Eur. J. Clin. Pharmacol., vol. 66, No. 6, pp. 537-545, 2010.

"Emerging Trends and Alerts." [Online]. Available: https:llwww. drugabuse.gov/drugsabuselemerging-trends-alerts. [Accessed: Sep. 7, 2018].

* cited by examiner

METHODS AND DEVICES THAT CHANGE COLOR TO INDICATE THE PRESENCE OF OPIOIDS AND OTHER NARCOTICS

CROSS-REFERENCE TO RELATED APPLICATIONS

This application claims the benefit of U.S. Provisional Patent Application No. 62/696,484, filed Jul. 11, 2018, which is incorporated herein by reference.

FIELD OF THE INVENTION

The present invention generally resides in the field of methods and devices that change color to indicate the presence of opioids and other amine-containing drugs.

BACKGROUND OF THE INVENTION

According to the Center for Disease Control (CDC), over one hundred people died every day of 2016 from opioid overdose, accounting for more than 42,000 opioid related deaths in the U.S. that year alone. The annual increase in opioid addiction has been highest in Ohio and New Hampshire, with opioid overdoses increasing 70% from July 2016 to September 2017. First responders to the scenes of these overdoses must be extremely cautious of inadvertent exposure to these potent opioid substances. For instance, carfentanyl has a lethal dose of about 2 milligrams (mg), and thus, particles that inadvertently come in contact with law enforcement, emergency medical services, firefighters, and other first responders could be fatal. In spite of the significant risk, there is currently no quick, cost-effective and rapid technology that enables a first responder to make a confident determination of the hazardous nature of a suspicious drug. Existing technologies for detecting the presence of opioids include Raman/IR detectors and 'spot test' kits. Raman and IR detectors are very accurate and can identify samples from a safe distance and without opening the packaging. However, the high cost of these hand-held detectors (~$20,000) prevents their deployment to every first responder.

Drug detection tests, sometimes referred to as spot tests, have been designed to differentiate between various opioids, amphetamines and other illicit drugs. These tests have been developed, modified and optimized to identify closely related classes of illicit drugs and are very useful in the prosecution of a crime. The Marquis reagent, for example, may be employed for the detection of morphine and other alkaloids, which show a red-violet color. This test has also been used as a general screening test for many drugs including various types of amphetamines. Several other tests such as Simon's reagent (for secondary amines), Mecke (for opium alkaloids), Liebermann's (for phenols), Fast blue (for cannabinoids), and Zwikker (for barbiturates) have been developed. These reagents are designed to react with functional groups of the drugs to form color compounds.

Currently, the most common drug detection tests come in the form of kits that include pouches that contain various ampules. The user must pick up and transfer the suspected drug to the pouch and break the various ampules to initiate a reaction. The solution changes color and the color itself can be used to identify the drug. These methods can be highly accurate and reproducible. However, these methods require the user to pick up the drug, and this puts the user in danger of exposure that may be potentially fatal in case of highly lethal drugs like carfentanyl. This causes undue safety issues to the first responder who has to carry out the test on-site under high stress conditions. Other drug detection products use a similar technology along with an applicator or sample collection surface.

Current wipe-based products use a cobalt thiocanate dye to indicate, by color change, contact with cocaine. Unfortunately, cobalt thiocyanate is toxic, and these wipe products cannot be used on surfaces that may come into human contact.

Other products that are available include test pens. The technology is based on antigen-enzyme binding. The small applicator tip of the pen also restricts detection of drugs on large surfaces. Also, aerosolized sprays are also available that that are also based upon antigen-enzyme binding technology. However, products that rely upon antigen-enzyme binding technology are relatively expensive.

There exists a need for a process and affordable product that allows for the rapid detection of dangerous opioids.

SUMMARY OF THE INVENTION

Advantageously, the present invention is based upon the discovery that certain dyes may be used to detect opioids and other amine-containing drugs. More specifically, the addition of certain dyes to various substrates may be used to indicate the presence of amine-containing drugs. These dyes provide a color change in response to the presence of amine-containing drugs that is visible to the unaided eye. The dye may be coated onto a wipe, and then the wipe may be simply contacted with a surface suspected of harboring a target analyte, i.e. a amine-containing drug. The wipe will change color if a target analyte is present.

One or more embodiments of the present invention provides a detection device for detecting a target analyte on a surface, the device comprising a substrate and a dye that produces a visible color change upon exposure to an opioid or other amine-containing drug.

One or more embodiments of the present invention provides a method for detecting a target analyte on a surface, the method comprising contacting a surface that is suspected of containing a target analyte with a drug detection device that includes a substrate and a dye that is capable of producing a visible color change upon contact with the target analyte.

DETAILED DESCRIPTION OF ILLUSTRATIVE EMBODIMENTS

The present invention provides a drug detection device, and a method for rapid detection of opioids and other amine-containing drugs on a surface. The drug detection device includes a substrate and a dye.

Substrate

Suitable substrates provide a solid support for the dye, and may be selected from a wide variety of materials. The form of the substrate is not particularly limited. In one or more embodiments, the drug detection device may be formulated as a wipe, a swab, or a glove.

Substrates suitable include films, woven and nonwoven fabrics, cellulosic substrates such as tissues, paper towels, coform materials, airlaid materials, bonded-carded webs, and the like. Nonexclusive examples of substrates are described in U.S. Pat. Nos. 4,775,582 and 4,853,281, 4,833, 003, and 4,511,488, all of which are incorporated herein by reference. In one or more embodiments, the substrate may be in the form of a wipe, a swab, or a glove. In one or more embodiments, the substrate may also be referred to as a mat.

In one or more embodiments, the substrate is a coherent fibrous sheet. The fibrous sheets may comprise natural fibers (e.g. wood pulp, cotton, bamboo, hemp, etc.), synthetic fibers (e.g. polyolefin, polyester, polyamide, polylactic acid, rayon, lyocell, etc.) or combinations of natural and synthetic fibers.

In one or more embodiments, the substrate comprises a polyester amide polymer having pendant functional groups, as described in U.S. Pat. No. 9,593,201, which is incorporated by reference herein. In one or more embodiments, the identity of the pendant groups in the polyester polymer influence the wetting nature of the substrate, which in turn influences the pick-up efficiency of the substrate. The pendant groups in the functional polyester may also influence interactions with the opioid analyte, and hence the pendant groups can be used to modulate reaction times and discriminate between different classes of analytes such as heroin and fentanyl. Advantageously, the functional polyester may be selected to favorably enhance the technology for binding of drug particles, modulation of response time, and color/tint of the substrate after contact with the opioid. By varying the pendant functional groups, the polymer fibers may be tailored for wettability, interactions with the silica particles and the response time of the color change.

In one or more embodiments, the substrate may comprise an air-laid nonwoven web. Examples include meltblown, spunbond, and bonded-carded web materials. Air-laid nonwoven sheets, and methods of making the same, are described in U.S. Pat. Nos. 3,849,241, 4,340,563, 4,443,513, 4,548,856, 4,853,281, 5,382,400, 5,575,874, 6,224,977, 6,811,638, 6,946,413, and U.S. Pat. App. Pub. Nos. 2004/0192136 A1 and 2006/0008621 A1, all of which are incorporated herein by reference.

In one or more embodiments, the substrate may comprise a coform nonwoven webs. Coform nonwoven webs may be formed by the comingling of polymeric fibers and absorbent fibers, such as polyolefin fibers and cellulosic fibers, as the fibers are entrained by a common airstream before they are deposited onto a forming surface. Coform sheet materials are described U.S. Pat. Nos. 4,100,324 and 5,350,624, and U.S. Pat. App. Pub. Nos. 2011/151596 A1, all of which are incorporated herein by reference. In one or more embodiments, the coform sheet may comprise a matrix of thermoplastic polymeric meltblown fibers and wood pulp fibers. Various suitable materials may be used to provide the polymeric meltblown fibers, such as, for example, polypropylene microfibers. In one or more embodiments, the polymeric meltblown fibers may be elastomeric fibers formed from elastomeric resins such as, for example, VISTAMAXX elastic olefin copolymer resin (available from ExxonMobil Corporation) or KRATON G styrene-ethylene/butylene-styrene and styrene-ethylene/propylene-styrene polymer resins (available from Kraton Performance Polymers, Inc.).

In one or more embodiments, the substrate may comprise hydroentangled nonwoven sheet materials. Hydroentangled nonwoven webs are sometimes referred to as spunlace fabrics. In certain aspects, hydroentangling readily allows for the combination of different fiber types, such as combining fibers of distinct composition (e.g. polymeric fibers and wood pulp fibers) or fibers of different sizes. Hydroentangled materials, and methods of making the same, are described U.S. Pat. Nos. 3,485,706, 3,620,903, 5,009,747, 5,284,703, and 6,200,669, all of which are incorporated herein by reference.

In one or more embodiments, the substrate may comprise a water dispersible and/or biodegradable sheet material. Examples of dispersible and/or degradable nonwoven fibrous materials are described in U.S. Pat. Nos. 5,667,635, 6,750,163, and 6,960,371, and U.S. Pat. App. Pub. No. 2017/0233912 A1, all of which are incorporated herein by reference.

In one or more embodiments, the substrate of the drug detection device may further include one or more optional ingredients selected from, but not limited to, color enhancers, catalysts, mechanical property modifiers, optical brighteners, anti-static agents, flame retardants, lubricants, wetting agents, softeners, mordants, and inorganic additives. The optional ingredients may be embedded within, absorbed into, dispersed upon or within, or coated upon the substrate. Chemicals and additives that are typically employed in dyeing processes and methods may be employed with the drug detection device of the present invention, including one or more of soda ash fixer, urea, Dharma dye fixative, Synthrapol, Dharma professional textile detergent, Milsoft, sodium alginate, Superclear, Calsolene oil, Bleach-Stop, Dharma color remover, optic whitener, ammonium sulfate, Jacquard silk salt, Retayne, Ludigal F, Dharma discharge paste, alum, potassium alum, and Fiber etch.

In one or more embodiments, the drug detection device includes titanium dioxide. The titanium dioxide may advantageously function as an optical brightener in the drug detection device of the present invention.

Inorganic additives include zeolites, alumina and silica. Advantageously, in one or more embodiments, inorganic additives may be selected to increase the selectivity of the opioid detection device. In one or more embodiments, the substrate may be a composite of an inorganic-polymer matrix embedded with one or more chemicals to provide indication of the presence of opioids. In one or more embodiments, the substrate may be fabricated from polymers and silica particles.

Examples of mordants include aluminum acetate, titanium oxalate, alum, iron salts, copper salts, tin salts, siloxanes, acrylates, sodium chloride, chrome alum, tannins, vinegar, baking soda, tara powder, cream of tartar, washing soda, tannic acid, certain salts of aluminum, chromium, copper, iron, iodine, potassium, sodium, tungsten, and tin, and combinations of any of the above.

The substrate should have sufficient mechanical strength and good processability, and should not be soluble in alcoholic or aqueous medium.

In one or more embodiments, the substrate has a polarity that is sufficient to interact with the dye, such that they dye does not leach out during processing or use of the opioid detection device.

In one or more embodiments, the substrate is characterized by a dry basis weight of from about 25 g/m$^2$ to about 420 g/m$^2$, in other embodiments, from about 30 g/m$^2$ to about 300 g/m$^2$, in other embodiments, from about 35 g/m$^2$ to about 250 g/m$^2$, in other embodiments, from about 40 g/m$^2$ to about 200 g/m$^2$, in other embodiments, from about 45 g/m$^2$ to about 150 g/m$^2$, and in still further embodiments, from about 50 g/m$^2$ to about 125 g/m$^2$.

In one or more embodiments, the substrate may be a porous substrate, where porous refers to the ability of the substrate to absorb liquid. The porous structure is advantageous because: (1) it allows for efficient encapsulation of dyes that are responsible for the color change response upon contact with the opioid, (2) the retention of moisture is more efficient and (3) higher adsorption of the opioid particles to the mats.

In one or more embodiments, the substrate may be a multi-layer substrate, where at least one layer of the substrate is porous.

In other embodiments, the substrate is non-porous and impermeable to the amine-containing drugs and other harmful substances. For example, when the drug detection device is a glove, a non-porous and impermeable substrate is advantageous because it protects the user from direct contact with potentially harmful substances.

If desired, the substrate may be further treated by one or more techniques as is known in the art to improve the durability, strength, hand, aesthetics, texture, and/or other properties of the substrate material. For instance, a nonwoven web may be pattern bonded or embossed by the use of heat, pressure and/or ultrasonic energy. The nonwoven substrate materials may be bonded by continuous and/or discontinuous lines, by patterns of numerous discrete elements, or other patterns as may be desired. In one or more embodiments, the nonwoven web may be bonded along the periphery of the sheet or simply across the width or cross direction of the web adjacent to the edges.

In these or other embodiments, a resin, latex or adhesive may be applied to the substrate by, for example, spraying or printing, to achieve the desired nature and degree of bonding. In one or more embodiments, the substrate may be treated by various other known techniques such as, for example, stretching, needling, creping, printing, dyeing, and so forth.

In one or more embodiments, the fibrous sheets may be used to form laminates with one or more additional sheet materials.

Dyes—

The drug detection device of the present invention further comprises a dye. In one or more embodiments, the dye enables detection of the presence of one or more opioids and other amine-containing drugs. In one or more embodiments, the dye enables differentiation between one or more opioids and other amine-containing drugs. That is, in one or more embodiments, the dye enables the identification of a specific drug. In one or more embodiments, the dye undergoes a color change in the presence of an opioid or other amine-containing drug. Advantageously, the color change is rapid and easily visible to the human eye. In one or more embodiments, the color change occurs in less than 1 minute, in other embodiments, in less than 30 seconds and in other embodiments, in less than 3 seconds. In one or more embodiments, the color change is virtually instantaneous.

In one or more embodiments, the dye is selected from the group consisting of malachite green oxalate, brilliant green, eosin yellowish, erythrosine b, methyl green, methyl violet, picric acid, crystal violet, bromocresol green, m-cresol purple, thymol blue, p-xylenol blue, cresol red, eosin bluish, quinaldine red, 2,4-dinitro phenol, 4-(dimethylamino) azobenzol, bromochlorophenol blue, bromophenol blue, congo red, methyl orange, 1-naphtholphthalein, m-cresol purple, thymol blue, p-xylenol blue, phenolphthalein, thymolphthalein, alkali blue, alizarin yellow gg, indigo carmine, epsilon blue, 2,5-dinitrophenol, alizarin sulphonic acid, methyl red, chlorophenol red, litmus, bromocresol purple, bromophenol red, 4-nitrophenol, bromoxylenol blue, bromothymol blue, phenol red, 3-nitrophenol, neutral red, and titan yellow.

Preparation

The desired dye may be coated onto a substrate in any of the commonly used methods for coating substrates, such as dip and nip, spraying, ink jet printing, etc. The dye may also be physically adsorbed or covalently conjugated onto latex, silica, cellulosic fibers or other polymeric fibers, which may be placed on or in the substrate generally or in a pattern.

Pre-Treatment

In one or more embodiments, the substrate may be pre-treated prior to applying the dye pre-mix. Any of the optional ingredients discussed above for the substrate may be applied in a pre-treatment step.

Dye Pre-Mix

In one or more embodiments, a dye pre-mix is prepared by dissolving or suspending the dye in a solvent. Suitable solvents include water and aqueous-based solvents, $C_{1-6}$ alcohols, glycols, and combinations thereof. In one or more embodiments, the solvent comprises water, ethanol, methanol, or a combination thereof.

In one or more embodiments, the dye pre-mix may further include one or more optional ingredients selected from, but not limited to, color enhancers, catalysts, mechanical property modifiers, optical brighteners, anti-static agents, flame retardants, lubricants, wetting agents, softeners, mordants, and inorganic additives. In one or more embodiments, one or more optional ingredients may be selected to provide a desired pH or ionic strength.

Dry Device Preparation

In one or more embodiments, the drug detection device is prepared by a method that includes the steps of (1) preparing a dye pre-mix by dissolving or mixing a dye with a solvent; (2) applying the dye pre-mix to a substrate; (3) removing the solvent. In one or more embodiments, the solvent may be removed through evaporation. In one or more embodiments, the step of removing the solvent may be accomplished with heating. In one or more embodiments, the step of removing the solvent may be accomplished in a vacuum chamber. In one or more embodiments, the step of removing the solvent may be accomplished at room temperature and pressure.

Wet Device Preparation

In other embodiments, the drug detection device is prepared by a method that includes the first two steps of the above method, namely, (1) preparing a dye pre-mix by dissolving or mixing a dye with a solvent; and (2) applying the dye pre-mix to a substrate. However, rather than removing the solvent to form a dry device, at least some of the liquid is left on the device, such that the device is moist. The moist device may then be enclosed in an airtight package for storage and/or shipment. The package may be opened before use.

In one or more embodiments, the amount of dye is at least an amount that is sufficient to produce a change in color upon contact with an opioid, where the color change is detectable to the unaided eye. In one or more embodiments, the amount of dye is at least about 0.01, in other embodiments, at least about 0.05, and in other embodiments, at least about 0.1 wt. %, based upon the total weight of the substrate and dye, on a dry basis. In one or more embodiments, the amount of dye is from about 0.01 to about 10 wt. %, in other embodiments, from about 0.05 to about 5, and in other embodiments, from about 0.1 to about 3 wt. %, based upon the total weight of the substrate and dye, on a dry basis.

Post-Treatment

In one or more embodiments, the substrate may be post-treated after applying the dye pre-mix. Any of the optional ingredients discussed above for the substrate may be applied in a post-treatment step.

In one or more embodiments of either of the above dry and wet methods of preparation, a subsequent washing step may follow the step of applying the dye pre-mix to the substrate. In one or more embodiments, the dye may be fixed onto the substrate by washing the dye/substrate with a fixative, detergent, wetting agent, surfactant, or combination thereof. Examples of fixatives include detergents such as Synthrapol SP and Retayne.

Method of Use

The drug detection device of the present invention is useful to indicate the presence of an opioid or other amine-containing drug, i.e. a target analyte. Thus, the present invention also provides a method for detecting a target analyte on a suspected surface. The method includes the steps of contacting a surface that is suspected of containing a target analyte with a drug detection device that includes a substrate carrying a dye that is capable of producing a visible color change to at least a portion of the substrate upon exposure to the target analyte. The target analytes, substrates, dyes, and color changes are as described herein.

In one or more embodiments, applying a wetting agent to either or both of the drug detection device and the suspected surface prior to contact facilitates the reaction of the target analyte and the dye, and thus speeds up and/or enhances the color change. In one or more embodiments, the method of the present invention includes the step of applying a wetting agent to the suspected surface prior to the step of contacting the surface with the drug detection device. In these or other embodiments, the method of the present invention includes the step of applying a wetting agent to the drug detection device prior to the step of contacting the surface with the drug detection device. In these or other embodiments, the drug detection device includes a wetting agent, and is provided in a sealed, airtight package or container. The method of the present invention may further include the step of removing the drug detection device from the airtight package prior to use. In one or more embodiments, the wetting agent is non-toxic. In one or more embodiments, the wetting agent is an aqueous wetting agent. In one or more embodiments, the wetting agent comprises water, a $C_{1-6}$ alcohol, such as methanol, ethanol, propanol, isopropanol, or a combination thereof.

In one or more embodiments, the drug detection device may be in the nature of a wipe, sheet, mat, swab or glove. As further described hereinbelow, a user may simply bring the drug device into contact with a suspected surface. In one or more embodiments, all of the surfaces of the substrate may be uniform in terms of the ability of the surface to change color. In these embodiments, any portion of the substrate may be employed in the method of use. In other embodiments, one or more portion of the surfaces of the substrate may be configured to change color. The portion of the substrate that is configured to change color upon contact with an opioid or other amine-containing drug may be referred to as the color-changing portion. For purposes of this specification, reference to a change of color for the drug detection device should be interpreted to mean a change of color for at least the color-changing portion of the device.

If a target analyte, i.e. an opioid or other amine-containing drug, is present on the suspected surface, the detection device, or at least the color-changing portion of the device, will change color.

In one or more embodiments, the drug detection device may originally be blue color, and upon contact with a target analyte, the target analyte reacts with the dye and the detection device becomes white. In one or more embodiments, contact with a target analyte results in a color change from orange to green. In one or more embodiments, contact with a target analyte results in a color change from orange to blue. In one or more embodiments, contact with a target analyte results in a color change from blood red to yellow. In one or more embodiments, contact with a target analyte results in a color change from blood red to white. In one or more embodiments, contact with a target analyte results in a color change from red to blood red. In one or more embodiments, contact with a target analyte results in a color change from white or off-white to blue.

Advantageously, the change in color may be virtually instantaneous, and does not require any additional heating, or addition of acids or bases. In one or more embodiments, the color change is readily visible and can be discerned by the human eye.

Target Analytes

Target analytes (the substance to be detected by the drug detector device) that may be detected by the drug detection devices and methods of the present invention include opioids and other amine-containing drugs. Many of these substances are used medically for pain relief, can be addictive, and are controlled substances. Overexposure may result in a fatal overdose. Examples include opiates, which refers to drugs that can be derived from opium. Specific examples of opioids and other amine-containing drugs include morphine, semi-synthetic and synthetic drugs such as hydrocodone, oxycodone, fentanyl, carfentanyl, acetyl fentanyl, tetrahydrofuran fentanyl, cocaine, methamphetamine and their analogues, as well as drug antagonists such as naloxone, and endogenous peptides such as the endorphins. In one or more embodiments, the target analyte includes heroin, fentanyl, oxycodone (OxyContin®), hydrocodone (Vicodin®), codeine, morphine, or a mixture or derivative thereof. In one or more embodiments, the target analyte includes one or more tertiary amine groups.

Advantageously, one or more embodiments of the present invention provide a safe and reliable way for first responders to detect the presence of opioids and other amine-containing drugs, thus providing a warning to avoid inadvertent exposure to potentially lethal drugs. The drug detector devices of the present invention are cost-effective and easy-to-use. In certain embodiments, where the drug detector device is a wipe or glove, large surface areas may be tested, such as table tops, cars, prison cells, etc. In other embodiments, the drug detector device is a swab that is adapted for hard to reach areas such as car consoles, pant pockets, etc. Microgram amounts of the target analyte can be detected. The drug detector device may be carried safely in a patrol car, an ambulance or on a person.

EXAMPLES

Cellulose Mats

Various cellulose-based polymers and copolymers were employed as substrates to prepare the drug detection devices. In one embodiment, cotton-based fabric mats of various compositions were obtained from a commercial source. Each mat was coated by soaking it in a dye solution. The mats were soaked in a dye/ethanol solution overnight or for twenty-four hours. The mats were then taken out and vacuum dried overnight. A concentration of 1 mg/mL was employed for the dye solution.

The dye-coated mats were tested for detection of fentanyl, acetyl fentanyl, cocaine, and morphine. In one embodiment, the target analyte was dissolved in water and transferred to a mat using a capillary tube. A small drop of the analyte solution instantaneously produced a color change for fentanyl, acetal fentanyl, morphine, and cocaine.

In another embodiment, the dye-coated mat was tested by wetting the mat using water and wiping the mat across a drug-containing surface. A color change was observed for cocaine, morphine, fentanyl, and acetyl fentanyl.

Polymer-Silica Composites

Electrospun polymer matrices-silica composites were also employed as substrates. The electrospun mats were prepared from functionalized polyester polymers as described in U.S. Pat. No. 9,593,201. In one embodiment, the surface of the substrate comprised silica particles and was stained with a dye. Advantages observed for this format were rapid reaction time (less than 3 seconds) and a readily visible color change upon contact with the analyte. In another embodiment, the substrate comprised an electrospun mat containing silica and a dye. A readily visible color change was observed within about 30 seconds of contact with an analyte.

In addition to the formats described above, the polymers can be fabricated into various formats such as scaffolds, films, hydrogels and electrospun mats. In addition, the polymers can also be dip-coated or solution-coated onto existing nitrile gloves or other substrates suitable for collection of samples.

Various modifications and alterations that do not depart from the scope and spirit of this invention will become apparent to those skilled in the art. This invention is not to be duly limited to the illustrative embodiments set forth herein.

What is claimed is:

1. A detection device for detecting a target analyte on a surface, the detection device comprising
a porous fabric substrate capable of absorbing liquid; and
a dye that produces a visible color change upon exposure to an opioid or other amine-containing drug, wherein the dye is selected from the group consisting of malachite green oxalate, brilliant green, erythrosine b, methyl green, methyl violet, picric acid, cresol red, crystal violet, m-cresol purple, thymol blue, bromocresol green, cresol red, p-xylenol blue, eosin bluish, quinaldine red, 4-(dimethylamino) azobenzol, methyl orange, 1-naphtholphthalein, m-cresol purple, thymol blue, p-xylenol blue, thymolphthalein, alkali blue, alizarin yellow gg, indigo carmine, epsilon blue, titan yellow, and bromocresol purple,
wherein the dye is either within the substrate or coated on the substrate or both within the substrate and coated on the substrate, and wherein the detection device is non-toxic to humans.

2. The detection device of claim 1, wherein the dye is selected from the group consisting of cresol red, m-cresol purple, bromocresol green, and bromocresol purple, wherein the amine-containing drug is characterized as one or more of a medical drug for pain relief and an illicit drug.

3. The detection device of claim 1, wherein the target analyte is selected from the group consisting of morphine, hydrocodone, oxycodone, fentanyl, carfentanyl, naloxone, endorphins, heroin, codeine, cocaine, and mixtures and derivatives thereof, and wherein the visible color change upon exposure to an opioid or other amine-containing drug can occur without any additional heating and without the addition of an acid or a base.

4. The detection device of claim 1, wherein the substrate comprises a woven fabric, a nonwoven fabric, a cellulose tissue, a paper towel, a coform material, an airlaid material, a polyester amide polymer having pendant functional groups, or a bonded-carded web, wherein the substrate is in the form of a wipe, a glove, or a swab.

5. The detection device of claim 1, wherein the substrate comprises natural fibers, synthetic fibers, or combinations thereof.

6. The detection device of claim 1, wherein the substrate comprises fibers selected from the group consisting of wood pulp, cotton, bamboo, hemp, polyolefin, polyester, polyamide, polylactic acid, rayon, lyocell, and combinations thereof.

7. The detection device of claim 1, wherein the substrate is in the form of a wipe, a swab, or a glove.

8. The detection device of claim 1, wherein the detection device further includes one or more optional ingredients selected from the group consisting of color enhancers, catalysts, mechanical property modifiers, optical brighteners, anti-static agents, flame retardants, lubricants, wetting agents, softeners, mordants, and inorganic additives.

9. The detection device of claim 1, wherein the detection device further comprises a wetting agent.

10. The detection device of claim 1, wherein the detection device is sealed in an airtight package.

11. A method for detecting a target analyte on a surface, the method comprising
contacting a surface that is suspected of containing a target analyte with a drug detection device, where the drug detection device includes
a porous fabric substrate capable of absorbing liquid, and
a dye that is capable of producing a visible color change upon the contact with the target analyte, wherein the dye is selected from the group consisting of malachite green oxalate, brilliant green, erythrosine b, methyl green, methyl violet, picric acid, cresol red, crystal violet, m-cresol purple, thymol blue, bromocresol green, cresol red, p-xylenol blue, eosin bluish, quinaldine red, 4-(dimethylamino) azobenzol, methyl orange, 1-naphtholphthalein, m-cresol purple, thymol blue, p-xylenol blue, thymolphthalein, alkali blue, alizarin yellow gg, indigo carmine, epsilon blue, titan yellow, and bromocresol purple,
wherein the dye is either within the substrate or coated on the substrate or both within the substrate and coated on the substrate.

12. The method of claim 11, wherein the method further comprises applying a wetting agent to either or both of the drug detection device or the surface that is suspected of containing a target analyte, prior to the step of contacting.

13. The method of claim 11, further comprising steps of
providing the detection device sealed in an airtight package, prior to the step of contacting;
removing the detection device from the airtight package, prior to the step of contacting; and
visually inspecting the drug detection device after the step of contacting, to determine if any portion of the drug detection device has changed color.

14. The method of claim 11, wherein at least a portion of the drug detection device undergoes a visible color change within about 30 seconds of the contact with the target analyte, wherein the visible color change occurs without any additional heating and without the addition of an acid or a base.

15. The method of claim 11, wherein at least a portion of the drug detection device undergoes a visible color change within about 5 seconds of the contact with the target analyte, wherein the visible color change occurs without any additional heating and without the addition of an acid or a base.

16. The method of claim 11, wherein the dye is selected from the group consisting of cresol red, m-cresol purple, bromocresol green, and bromocresol purple.

17. The method of claim 11, wherein the target analyte is an amine-containing drug, and wherein the method does not require a user to pick up the target analyte, wherein the amine-containing drug is characterized as one or more of a medical drug for pain relief and an illicit drug.

18. The method of claim 11, wherein the target analyte is selected from the group consisting of morphine, hydrocodone, oxycodone, fentanyl, carfentanyl, naloxone, endorphins, heroin, codeine, cocaine, and mixtures and derivatives thereof.

19. The method of claim 11, wherein the substrate comprises a woven fabric, a nonwoven fabric, a cellulose tissue, a paper towel, a coform material, an airlaid material, a polyester amide polymer having pendant functional groups, or a bonded-carded web.

20. A detection device for detecting a target analyte on a surface, the detection device comprising a substrate, wherein the substrate is selected from the group consisting of a wipe, a glove, and a swab; and a dye that produces a visible color change upon exposure to an opioid or other amine-containing drug, wherein the dye is selected from the group consisting of malachite green oxalate, brilliant green, erythrosine b, methyl green, methyl violet, picric acid, cresol red, crystal violet, m-cresol purple, thymol blue, bromocresol green, cresol red, p-xylenol blue, eosin bluish, quinaldine red, 4-(dimethylamino) azobenzol, methyl orange, 1-naphtholphthalein, m-cresol purple, thymol blue, p-xylenol blue, thymolphthalein, alkali blue, alizarin yellow gg, indigo carmine, epsilon blue, titan yellow, and bromocresol purple, wherein the dye is either within the substrate or coated on the substrate or both within the substrate and coated on the substrate, wherein the detection device is non-toxic to humans, and wherein the visible color change upon exposure to an opioid or other amine-containing drug can occur without any additional heating and without the addition of an acid or a base.

* * * * *